United States Patent
Hobot et al.

(10) Patent No.: US 10,583,235 B2
(45) Date of Patent: Mar. 10, 2020

(54) CUSTOMIZED DIALYSATE SOLUTION USING SPIKES

(71) Applicant: Medtronic, Inc., Minneapolis, MN (US)

(72) Inventors: Christopher M. Hobot, Rogers, MN (US); Martin T. Gerber, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 273 days.

(21) Appl. No.: 15/582,830

(22) Filed: May 1, 2017

(65) Prior Publication Data

US 2017/0319766 A1    Nov. 9, 2017

Related U.S. Application Data

(60) Provisional application No. 62/332,238, filed on May 5, 2016.

(51) Int. Cl.
| | |
|---|---|
| *A61M 1/16* | (2006.01) |
| *A61K 33/00* | (2006.01) |
| *A61K 33/06* | (2006.01) |
| *A61K 31/7004* | (2006.01) |

(52) U.S. Cl.
CPC ....... *A61M 1/1656* (2013.01); *A61K 31/7004* (2013.01); *A61K 33/00* (2013.01); *A61K 33/06* (2013.01); *A61M 1/1601* (2014.02); *A61M 1/1603* (2014.02); *A61M 1/1605* (2014.02); *A61M 1/1613* (2014.02); *A61M 1/1666* (2014.02); *A61M 1/1696* (2013.01); *A61M 2205/18* (2013.01)

(58) Field of Classification Search
CPC .... A61K 31/7004; A61K 33/00; A61K 33/06; A61M 1/1656; A61M 1/1666; A61M 1/1696; A61M 2205/18; A61M 1/1601; A61M 1/1603; A61M 1/1605; A61M 1/1613
See application file for complete search history.

(56) References Cited

U.S. PATENT DOCUMENTS

| | | | |
|---|---|---|---|
| 5,141,493 | A | 8/1992 | Jacobsen |
| 6,645,191 | B1 | 11/2003 | Knerr |
| 2012/0181230 | A1 | 7/2012 | Kloeffel |
| 2012/0273354 | A1 | 11/2012 | Orhan |

FOREIGN PATENT DOCUMENTS

| | | |
|---|---|---|
| DE | 3224823 | 1/1984 |
| WO | WO2011161056 | 12/2011 |

OTHER PUBLICATIONS

PCT/US2017/030377_ISR (dated Sep. 1, 2017 ).
PCT/US2017/030377_WO (dated Sep. 1, 2017).

*Primary Examiner* — John Kim
(74) *Attorney, Agent, or Firm* — Kenneth Collier; Roger Hahn (57) ABSTRACT

Systems and methods of generating a customized dialysate solution are provided. The system and methods use stock concentrates, with the addition of spikes to generate a customized dialysate solution based on the needs of the patient.

15 Claims, 2 Drawing Sheets

CUSTOMIZED DIALYSATE SOLUTION USING SPIKES

CROSS-REFERENCE TO RELATED APPLICATION

This application claims the benefit of and priority to U.S. Provisional Patent Application No. 62/332,238 filed May 5, 2016, the entire disclosure of which is incorporated by reference herein.

FIELD OF THE INVENTION

Systems and methods are provided for customizing buffers and dialysate based on specified requirements for a patient or group of patients. The systems and methods described can generate a dialysate from the specified requirements using dialysate components including base solutions or pre-set powder packets. The systems and methods can customize (or personalize) a resulting solution using additional pre-set powder packets or concentrate solutions to "spike" and generate a customized buffer or dialysate.

BACKGROUND

Sorbent cartridges operate by adsorbing ions and other waste species from a fluid, such as dialysate. In addition to removing wastes, such as urea, phosphates and non-polar molecules, sorbent cartridges remove non-waste ions from the dialysate, such as potassium, calcium and magnesium. Other substances, such as glucose, chloride and acetate may also be removed by the sorbent cartridge and replaced by an infusate system. Because non-waste ions are removed from the dialysate by the sorbent cartridge, these ions must be added back to the dialysate before the dialysate is recirculated to the dialyzer. Without the addition of these cations back into the dialysate, a large gradient would develop between the patient's blood and the dialysate in the dialyzer, resulting in increased removal of these ions from the patient and an inability to control the level of these ions in the patient's blood to meet treatment goals. However, known dialysis solutions oftentimes have fixed concentrate amounts that cannot be adjusted prior to dialysis. The use of standardized dialysate and the absence of any adjustment over time to match changes in residual kidney function can result in sub-optimal outcomes. Notably, a one-size-fits-all approach is not ideal for dialysis because many patients cannot effectively tolerate particular solutes or may require specific initial concentrate amounts. For example, certain patients cannot tolerate acetate while other dialysis patients may require glucose to prevent hypoglycemia.

A number of sudden deaths occurring during the initial dialysis of acutely ill patients has been blamed on hypokalemia and linked to failing to deliver dialysate having appropriate potassium concentrations (Replacement of Renal Function by Dialysis, Jacobs et al., Kluwer Academic Publishers, 1996 $4^{th}$ Ed.). Hypokalemia is a potentially life-threatening imbalance resulting from a rapid shift of potassium from the extracellular to the intracellular space that can occur during dialysis. Intensive dialysis in an average dialysis patient without severe metabolic acidosis can bring about hypokalemia even if a normal-potassium dialysate is used. Patients entering dialysis with a history suggesting hypokalemia receive a dialysate having a potassium concentration higher than normal. However, using modified dialysate may create a false sense of security so much so that a vigilant watch for the development of disease-associated hypokalemia is neglected (See id. at page 26, col. 2, lines 7-15). Similarly, calcium ions play a primary role in the contractile process of vascular smooth muscle and cardiac cells. Calcium imbalance can result in hyper- or hypo-calcemia. Acid-base status in dialysis patients is estimated from plasma bicarbonate wherein an inappropriate amount of bicarbonate can result in acidosis or alkalosis.

Known systems cannot provide high dilution factors because they lack sufficient accuracy to meter concentrates and cannot provide control over pumps to deliver necessary concentration amounts. Instead, known dialysis systems generate dialysate by adding large amounts °f concentrates to water to dilute the concentrates by a factor of around 34:1. As such, large volumes of concentrates are required to generate a necessary volume of dialysate for a dialysis session. Therefore, small components, low volume reservoirs, and compact system size cannot be provided in the known systems. Known systems also usually require a stock of many dialysate formulations to meet patient demand. Storage and management of a large number of different dialysate formulations can become cumbersome and costly. As a result, many clinics limit the available dialysate formulations to a few formulations resulting in sub-optimal treatment for patients.

Hence, there is a need for customizable dialysate and related systems and methods for preparation thereof. The need extends to systems and related methods for customization or personalization of the dialysate solution to a particular patient profile. The need includes pre-set amount of base concentrates that can be customized by spikes of concentrates that can be delivered in pre-set amounts and be automatically provided to reduce error. There is a further need for particular formulations of cations and other infusates that can be used based on the needs of each patient. There is a need for a system that allows clinics to stock only a small number of interchangeable components to allow broad customization of dialysate formulations to meet the varied needs of different patients. The need includes in-system sensors that can determine whether the specified dialysate formulations based on a patient's needs are being properly delivered. There is a need for systems and methods of controlling the pH and solute concentrations in a dialysate based on a dialysate prescription to ensure patient safety and effective dialysis treatment. There is a need for partially of fully automated systems and methods that minimize operator error.

There is also a need for a system that can use a high dilution factor to lower the size requirements of the concentrate reservoirs, resulting in compact concentrate reservoirs increasing the portability of the dialysis system. Hence, there is a need for customizing an amount of concentrates such as bicarbonate, calcium, magnesium, glucose, potassium among others, to be added to a dialysate. The need includes systems and methods for setting a required amount of concentrates in advance of a dialysis session. Alternatively, there is a need for customizing amounts of concentrates wherein the customization is not just for an individual, but can include a generalized patient profile or group of patient profiles.

SUMMARY OF THE INVENTION

The first aspect of the invention relates to a method for customizing a dialysate using spikes. In any embodiment of the first aspect of the invention, the method includes the steps of adding a base concentrate to a concentrate reservoir of a dialysate system wherein the base concentrate contains one or more of potassium, magnesium, calcium, and glucose; customizing a dialysate by adding one or more spikes to the concentrate reservoir containing the base concentrate wherein the spikes are selected from the group of potassium, magnesium, calcium, glucose, and combinations thereof; conveying fluid from the concentrate reservoir to a dialysate flow path at a set ratio to obtain a dialysate with a predetermined solute concentration based on a dialysate prescription; wherein the set ratio is a ratio of a dialysate flow rate to a concentrate flow rate; and sensing a conductivity of dialysate in the dialysate flow path downstream of the concentrate line using a sensor.

In any embodiment of the first aspect of the invention, the dialysate prescription is determined, at least in part, on a concentration of one or more solutes in a patient's blood.

In any embodiment of the first aspect of the invention, the dialysate prescription is determined, at least in part, on a dialysis outcome of a patient in one or more previous dialysis sessions.

In any embodiment of the first aspect of the invention, the set ratio of the dialysate flow rate to the concentrate flow rate is between any of 100:1 and 300:1, 100:1 and 250:1, 200:1 and 300:1, or 225:1 and 275:1.

In any embodiment of the first aspect of the invention, the base solution has potassium in a concentration of between 0 and 600 mmol/L, calcium in a concentration of between 0 and 900 mmol/L, magnesium in a concentration of between 37 and 115 mmol/L, and glucose in a concentration of between 0 and 600 mmol/L.

In any embodiment of the first aspect of the invention, the step of adding one or more spikes to the concentrate reservoir results in any one of: (a) an increase in dialysate potassium concentration of between 0.5 and 2 mmol/L; (b) an increase in dialysate calcium concentration of between 0.2 and 1 mmol/L; (c) an increase in dialysate magnesium concentration of between 0.1 and 0.3 mmol/L; or (d) an increase in dialysate glucose concentration of between 0.5 and 2 mmol/L.

In any embodiment of the first aspect of the invention, the method includes steps for determining an actual conductivity of the dialysate; comparing the actual conductivity of the dialysate to the dialysate prescription; and if the actual conductivity of the dialysate is lower than the dialysate prescription, adding one or more spikes to the concentrate reservoir.

In any embodiment of the first aspect of the invention, step of adding one or more spikes to the concentrate reservoir includes adding one or more powders to the concentrate reservoir.

In any embodiment of the first aspect of the invention, the step of adding one or more spikes to the concentrate reservoir includes adding one or more spike solutions to the concentrate reservoir.

In any embodiment of the first aspect of the invention, the step of adding a base concentrate to the concentrate reservoir includes adding a base solution to the concentrate reservoir.

In any embodiment of the first aspect of the invention, the step of adding a base concentrate to the concentrate reservoir includes dissolving a base powder in water.

Any of the features disclosed as being part of the first aspect of the invention can be included in the first aspect of the invention, either alone or in combination.

The second aspect of the invention relates to a dialysis system having a concentrate reservoir configured to contain a base concentrate solution wherein the concentrate reservoir is configured to receive one or more spikes and is fluidly connected to a dialysate flow path via a concentrate line, wherein the base concentrate contains one or more of potassium, magnesium, calcium, and glucose and wherein the spikes are selected from the group of potassium, magnesium, calcium, glucose, and combinations thereof; a concentrate pump for conveying fluid from the concentrate reservoir to the dialysate flow path; and a conductivity sensor in the dialysate flow path downstream of the concentrate line wherein the conductivity sensor determines a conductivity of dialysate in the dialysate flow path.

In any embodiment of the second aspect of the invention, the system has a processor for performing the method of the first aspect of the invention.

In any embodiment of the second aspect of the invention, the dialysate flow path has a dialysate pump; and a ratio of flow rates of the dialysate pump and concentrate pump is a set ratio.

In any embodiment of the second aspect of the invention, the ratio of flow rates of the dialysate pump and concentrate pump is between any of 100:1 and 300:1, 100:1 and 250:1, 200:1 and 300:1, or 225:1 and 275:1. Furthermore, all possible ranges between 100:1 and 300:1 are contemplated, e.g., 101:1 and 103:1; 298:1 and 299:1; and 101:1 and 299:1.

In any embodiment of the second aspect of the invention, the system provides an alert if the conductivity of a dialysate in the dialysate flow path differs from a dialysate prescription.

Any of the features disclosed as being part of the second aspect of the invention can be included in the second aspect of the invention, either alone or in combination.

The third aspect of the invention is drawn to a composition. In any embodiment of the third aspect of the invention, the composition includes a base concentrate selected from the group consisting of: (a) potassium in a concentration of between 400 mmol/L and 600 mmol/L; calcium in a concentration of between 600 mmol/L and 900 mmol/L; and magnesium in a concentration of between 150 mmol/L and 225 mmol/L; (b) potassium in a concentration of between 400 mmol/L and 600 mmol/L; and magnesium in a concentration of between 75 mmol/L and 112.5 mmol/L; (c) calcium in a concentration of between 200 mmol/L and 300 mmol/L; and magnesium in a concentration of between 75 mmol/L and 112.5 mmol/L; (d) potassium in a concentration of between 400 mmol/L and 600 mmol/L; calcium in a concentration of between 600 mmol/L and 900 mmol/L; magnesium in a concentration of between 75 mmol/L and 112.5 mmol/L; and glucose in a concentration of between 400 mmol/L and 600 mmol/L; (e) potassium in a concentration of between 200 mmol/L and 300 mmol/L; calcium in a concentration of between 600 mmol/L and 900 mmol/L; magnesium in a concentration of between 150 mmol/L and 225 mmol/L; and glucose in a concentration of between 400 mmol/L and 600 mmol/L; (f) potassium in a concentration of between 600 mmol/L and 900 mmol/L; calcium in a concentration of between 600 mmol/L and 900 mmol/L; magnesium in a concentration of between 150 mmol/L and 225 mmol/L; and glucose in a concentration of between 400 mmol/L and 600 mmol/L; and (g) potassium in a concentration of between 400 mmol/L and 600 mmol/L; magnesium in a concentration of between 150 mmol/L and 225 mmol/L; and glucose in a concentration of between 400 mmol/L and 600 mmol/L; as well as one or more spike selected from the group consisting of: (a) potassium in a concentration of between 200 mmol/L and 300 mmol/L; (b) calcium in a concentration of between 50 mmol/L and 75 mmol/L; (c) magnesium in a concentration of between 25 mmol/L and 37.5 mmol/L; and (d) glucose in a concentration of between 200 mmol/L and 300 mmol/L.

In any embodiment of the third aspect of the invention, for the treatment of a dialysis patient, one of the base concentrates is selected and optionally one or more of spikes is selected.

Any of the features disclosed as being part of the third aspect of the invention can be included in the third aspect of the invention, either alone or in combination.

DETAILED DESCRIPTION OF THE INVENTION

Unless defined otherwise, all technical and scientific terms used herein generally have the same meaning as commonly understood by one of ordinary skill in the relevant art.

The articles "a" and "an" are used herein to refer to one or to more than one (i.e., to at least one) of the grammatical object of the article. By way of example, "an element" means one element or more than one element.

The phrase "adding one or more spikes" refers to an addition of a spike or multiple spikes, as defined herein, to a stock concentrate.

The term "actual conductivity" refers to a conductivity of a fluid existing at a particular point in time, as opposed to a desired conductivity of the fluid.

The term "alert" refers to an audio, visual, or tactile cue of a system parameter.

A "base concentrate" refers to a solution or powder that when dissolved in a set amount of water will contain a set concentration of one or more solutes to be used in dialysis.

A "base powder" is one or more undissolved components of a dialysate that, when dissolved in a set amount of water, will result in a set concentration of one or more components.

A "base solution" is a solution of one or more solutes to be used in dialysis of a known concentration.

The terms "comparing" or to "compare" refers to a process for examining two values to determine whether the values are the same or different.

The term "comprising" includes, but is not limited to, whatever follows the word "comprising." Thus, use of the term indicates that the listed elements are required or mandatory but that other elements are optional and may or may not be present.

The term "concentrate flow rate" refers to the flow rate of a concentrate solution from a concentrate reservoir to a dialysate flow path.

The term "concentrate line" refers to a connector or fluid flow path that fluidly connects a concentrate reservoir to a dialysate flow path.

A "concentrate pump" is a pump positioned on a concentrate line for moving fluid from a concentrate reservoir to a dialysate flow path.

A "concentrate reservoir" is a container configured to contain a solution of one or more solutes, wherein the one or more solutes in the concentrate reservoir have a concentration greater than that to be used in dialysis.

The term "concentration of one or more solutes" refers to an amount of a solute(s) dissolved in a fluid per unit volume.

The term "conductivity" refers to the inverse of electrical resistance of a fluid.

A "conductivity sensor" is a sensor capable of determining the conductivity of a fluid.

The term "configured to contain" means any particular form, alignment, shape, design, marking, or arrangement suitable for allowing one container, component or material to be held within a second container or component.

The term "configured to receive" means any particular form, alignment, shape, design, marking, or arrangement suitable for allowing one container, component or material to be placed within a second container or component.

The term "consisting of" includes and is limited to whatever follows the phrase "consisting of" Thus, the phrase indicates that the limited elements are required or mandatory and that no other elements may be present.

The term "consisting essentially of" includes whatever follows the term "consisting essentially of" and additional elements, structures, acts or features that do not affect the basic operation of the apparatus, structure or method described.

The terms "conveying fluid" or to "convey fluid" refer to the process of moving a fluid through a flow path.

The terms "customizing" or "customized" refers to generating a composition or method based on the needs of a particular patient or a group of patients. The term is broader than "personalizing" or "personalized," which refer to generating a composition based on the needs of a specific individual. As such, "customizing" or "customized" is broader in scope and inclusive of the terms of "personalizing" or "personalized" modifying the compositions or methods of the present invention.

The terms "determining" or to "determine" refer to a process of sensing or calculating a value of one or more variables of a system.

A "dialysate flow path" is a route in which a fluid will travel during dialysis.

The term "dialysate flow rate" refers to a flow rate of dialysate in a dialysate flow path.

A "dialysate prescription" refers to the intended presence of and concentrations of solutes in a dialysate for a patient or a patient profile.

A "dialysate pump" is a pump positioned in a dialysate flow for moving fluid through a dialysate flow path.

A "dialysis session" is a time period a patient is treated by dialysis, hemodialysis, hemofiltration, ultrafiltration, or other blood fluid removal therapy.

The term "downstream" refers to a position of a first component in a flow path relative to a second component wherein fluid will pass by the second component prior to the first component during normal operation. The first component can be said to be "downstream" of the second component, while the second component is "upstream" of the first component.

The term "flow rate" refers to the volume of a fluid moving past a specific point per unit of time.

A "fluid" is a liquid substance optionally having a combination of gas and liquid phases in the fluid. Notably, a liquid, as used herein, can therefore also have a mixture of gas and liquid phases of matter.

The terms "fluid connection," "fluidly connectable" or "fluidly connected" refer to providing for the passage of fluid or gas from one point to another point. The two points can be within or between any one or more of compartments, modules, systems, components, and rechargers, all of any type.

"An increase in dialysate glucose concentration" refers to a change in a glucose concentration of the dialysate to a higher concentration.

"An increase in dialysate magnesium concentration" refers to a change in a magnesium concentration of the dialysate to a higher concentration.

"An increase in dialysate potassium concentration" refers to a change in a potassium concentration of the dialysate to a higher concentration.

The term "instructions" refers to a step or series of steps that when followed will achieve a set outcome.

The term "outcome of a patient in one or more previous dialysis sessions" refers to the physiological state of the patient during or after a previous dialysis session.

The term "powder" refers to matter in the solid state.

A "predetermined solute concentration" refers to a concentration of solutes in a fluid that is set before the fluid is generated.

The term "processor" as used herein is a broad term and is to be given its ordinary and customary meaning to a person of ordinary skill in the art. The term refers without limitation to a computer system, state machine, processor, or the like designed to perform arithmetic or logic operations using logic circuitry that responds to and processes the basic instructions that drive a computer. In any embodiment of the first, second, third, and fourth invention, the terms can include ROM ("read-only memory") and/or RAM ("random-access memory") associated therewith.

The terms "sensing" or to "sense" refer to the process of determining a characteristic of a system.

A "sensor" is a component capable of determining one or more states of one or more variables in a system.

The term "set ratio" refers to a predetermined relationship between two amounts relative to each other.

A "solute" is a substance that is dissolved in a solvent.

The terms "sorbent cartridge" and "sorbent container" refer to a cartridge containing one or more sorbent materials for removing specific solutes from solution, such as urea. The term "sorbent cartridge" does not require the contents in the cartridge be sorbent based, and the contents of the sorbent cartridge can be any contents that can remove waste products from a dialysate. In this connection, the sorbent cartridge may include any suitable amount of one or more sorbent materials. In certain instances, the term "sorbent cartridge" refers to a cartridge which includes one or more sorbent materials in addition to one or more other materials capable of removing waste products from dialysate. "Sorbent cartridge" can include configurations where at least some materials contained in the cartridge do not act by mechanisms of adsorption or absorption.

A "spike" is a powder containing one or more solutes to be used in dialysis. The spike can be added to a base concentrate to adjust the concentration of the one or more solutes in the base concentrate.

A "spike solution" is a concentrated solution of one or more solutes to be used in dialysis that can be added to a base concentrate to adjust the concentration of the one or more solutes in the base concentrate.

Infusate Compositions

Figure 1:
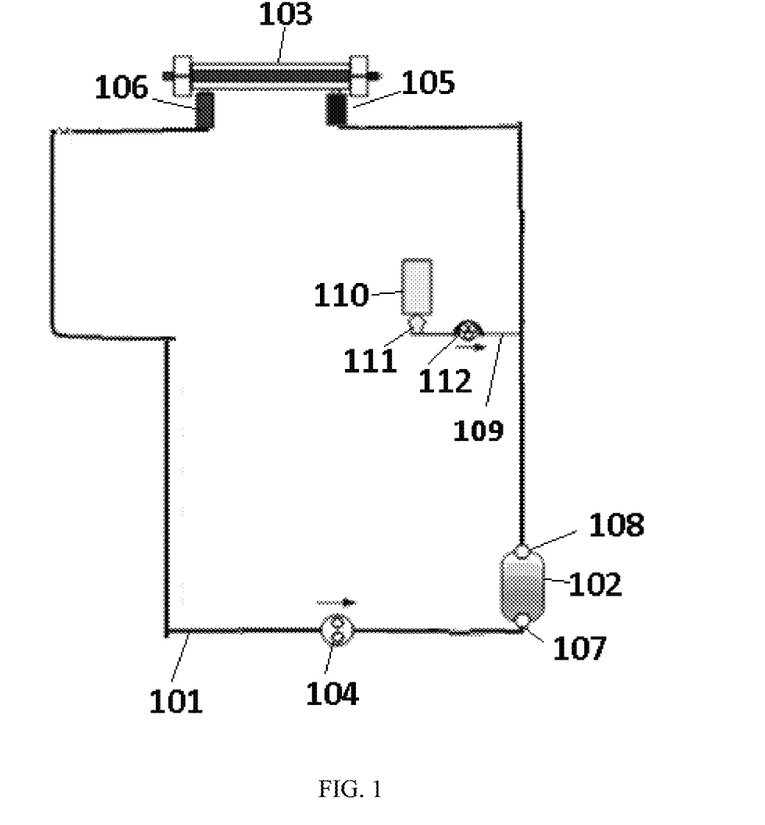
FIG. 1 shows a dialysate flow path for creating unique dialysate formulations.

The first, second, and third aspects of the invention relate to systems and methods for generating a customized dialysate from base concentrates and spikes. FIG. 1 shows a simplified version of a dialysis system using a sorbent cartridge. Dialysate customized to a particular patient can be said to be "customized" for a groups of patient profiles, or "personalized" to an individual patient. It will be understood that "customized" is broader in scope than "personalized" and encompasses "personalized" compositions. Management software can receive inputs from sensors determining the conductivity of the dialysate to ensure delivery of a specified dialysis prescription for a particular patient.

In FIG. 1, dialysate can be recirculated through dialysate flow path 101 containing sorbent cartridge 102 and dialyzer 103. Dialysate pump 104 provides a driving force for conveying the dialysate through dialysate flow path 101. Dialysate enters the dialyzer 103 through dialyzer inlet 105 and exits through dialyzer outlet 106. Contemporaneously, blood from a patient can be circulated through an extracorporeal circuit from the patient, through the dialyzer 103 and back to the patient. A blood pump can provide a driving force for conveying blood through the extracorporeal circuit. In dialyzer 103, ions and other species present in the blood can cross through a semi-permeable membrane (not shown) in the dialyzer 103 and into the dialysate, while solutes present in the dialysate can cross through the semi-permeable membrane and into the blood. Dialysate containing wastes from the blood of the patient can be passed through sorbent cartridge 102. Dialysate enters the sorbent cartridge 102 through sorbent cartridge inlet 107 and exits through sorbent cartridge outlet 108. In the sorbent cartridge 102, various sorbent materials can remove wastes from the dialysate so the dialysate can be returned to the dialyzer 103. The sorbent cartridge 102 can contain one more of activated carbon, urease, a cation exchange material and an anion exchange material. The activated carbon can absorb creatinine, glucose, uric acid, $\beta 2$-microglobulin and other non-ionic toxins. The urease catalyzes the breakdown of urea present in the dialysate into ammonium ions and carbon dioxide. The ammonium ions, as well as any other cations present, are removed from the fluid by the cation exchange material, such as zirconium phosphate. Anions, such as phosphates, can be removed from the fluid by the anion exchange material, such as zirconium oxide.

Because cations, such as potassium, calcium and magnesium are removed from the fluid by the zirconium phosphate or other cation exchange material, these cations must be added back into the dialysate before the dialysate reaches the dialyzer 103. Concentrate reservoir 110 can contain ions and other solutes such as potassium, calcium, magnesium, acetate and chloride ions, or glucose and other non-ionic solutes. Concentrate reservoir 110 can also be configured to contain one or more base concentrates containing solutes used in dialysis and to receive one or more spikes to adjust the solute concentration. Concentrate reservoir 110 can be positioned in the dialysate flow path 101 at a position downstream of the sorbent cartridge 102, so concentrates added to the dialysate flow path 101 are not removed from the dialysate prior to reaching the dialyzer 103.

The concentrates can be a concentrated infusate solution, which is added to the dialysate. The actual solute concentration of the concentrates and the pump flow rate of fluid from the concentrate reservoir 110 into the dialysate can determine the concentration of solutes in the resulting dialysate, as explained. Fluid from concentrate reservoir 110 can be selectively metered into the dialysate through concentrate line 109, which fluidly connects concentrate connector 111 to the dialysate flow path 101. Concentrate pump 112 can provide a driving force to convey fluid through concentrate line 109, and to control fluid movement through the concentrate line 109. Control over the rate of fluid movement through the flow through cartridge will provide control over the rate of concentrate addition for any given dialysate flow rate through the dialysate flow path 101. Concentrate reservoir 110 can be configured to hold a base concentrate solution and to receive one or more spikes to result in a customized dialysate.

The dialysate pump and concentrate pump can be any type of pumps known in the art capable of controlling the movement of fluid to maintain a set ratio of pump flow rates, including but not limited to gear pumps, peristaltic pumps, diaphragm pumps, and impeller pumps. One or more conductivity sensors can be positioned to detect the conductivity of the dialysate and/or the concentrate source 110, to compare the actual conductivity to the dialysate prescription, and to ensure a conductivity of the dialysate within a proper pre-set range. If the conductivity of the dialysate is not within a preset range of the dialysate prescription, the system can generate an alert or halt dialysis. The conductivity sensors can be provided on a separate sensor line (not shown in FIG. 1) or in the dialysate flow path 101. If conductivity sensors are provided on a separate or external sensor line, a small amount of dialysate can be drawn out of the dialysate flow path 101, and passed through the conductivity sensor to obtain a conductivity measurement. A valve (not shown in FIG. 1) can control the movement of fluid from the dialysate flow path 101 into the sensor line. One of skill in the art will understand that one or more sensors can be included in the system. The pre-set range can be set at a percentage relative to a dialysate prescription including between any of 5%-30%, 5%-10%, 5%-20%, 10%-20% or 20% to 30% deviation in conductivity relative to the dialysate prescription. One or more conductivity sensors can be placed downstream of the concentrate source to allow sensing of the dialysate after the concentrate has been added to the dialysate.

Dialysis can be halted if an actual conductivity of the dialysate is outside of a pre-set range. Halting dialysis can support patient safety by ensuring dialysis is not carried out using incorrect solute concentrations. The system can also generate an alert informing the user that incorrect solute concentrations are being used. The alert can further include user instructions to add one or more additional spikes to the concentrate reservoir if the sensors determine the conductivity of the dialysate is below a level required by the dialysate prescription. A control system or processor can also determine the type and number of spikes to add to the concentrate reservoir to return the conductivity of the dialysate to the conductivity set in the dialysate prescription.

Base concentrates can be provided pre-mixed in proper proportions and amounts in either powder or solution form. A user can user pre-mixed amounts to conveniently add a required amount of base concentrate solution to a concentrate reservoir to generate a dialysate having a set concentration of solutes. If the base concentrates are provided in solid or powdered form as a base powder, the user can generate the final concentrate solution by adding the solid or powdered concentrate to the concentrate reservoir. The concentrate reservoir can be sized such that only a set amount of water can be added to the concentrate reservoir, ensuring the user dissolves a correct amount of solid or powdered concentrates in a proper amount of water. The concentrate reservoir can include a line or other marking showing the proper amount of water to add in dissolving the solid or powdered concentrates. The spikes can be provided in solid or powdered form, and the user can generate the final concentrate solution by adding the solid or powdered spike to the concentrate reservoir. The spikes can also be provided as concentrated spike solutions, and the user can generate the final concentrate solution by adding the spike solution to the concentrate reservoir.

Spikes containing a single solute can be added to a solution to selectively adjust solute concentration to generate a customized dialysate. For example, a user can adjust the final dialysate composition to customize (or personalize) a dialysate per the particular needs of a patient or groups of patients using a select and limited number of different base concentrates. Table 1 provides sample concentrate compositions, showing non-limiting specified concentrations of solutes in the dialysate. Several options are available, depending on the needs of the particular patient and the dialysate prescription.

TABLE 1

| Concentrate Composition | $K^+$ mmol/L | $Ca^{2+}$ mmol/L | $Mg^{2+}$ mmol/L | Glucose (mmol/L) |
| --- | --- | --- | --- | --- |
| 1 | 2.0 | 1.5 | 0.375 | 0 |
| 2 | 2.0 | 0 | 0.375 | 0 |
| 3 | 0 | 1.0 | 0.375 | 0 |
| 4 | 2.0 | 1.5 | 0.375 | 2.0 |
| 5 | 1.0 | 1.5 | 0.375 | 2.0 |
| 6 | 3.0 | 1.5 | 0.375 | 2.0 |
| 7 | 2.0 | 0 | 0.375 | 2.0 |
| 8 | 1.0 | 0 | 0 | 0 |
| 9 | 0 | 0.25 | 0 | 0 |
| 10 | 0 | 0 | 0.125 | 0 |
| 11 | 0 | 0 | 0 | 1.0 |

Table 1 shows concentrate compositions 1-7 as base concentrates and compositions 8-11 as spikes. If a dialysate prescription requires a dialysate having a concentration of potassium of 4.0 mmol/L, a concentration of magnesium of 0.5 mmol/L, a concentration of calcium of 2.0 mmol/L, and a concentration of glucose of 1.0 mmol/L, a user can select base concentrate solution number 1 from Table 1. The user can then add to the base concentrate two spikes of composition number 8, two spikes of composition number 9, one spike of composition number 10, and one spike of composition number 11. By utilizing the base concentrate solutions and spikes, many permutations of dialysate compositions can be generated while only requiring storage of a few different compositions.

Table 1 also shows solute concentrations for specified concentrations of the solutes in the dialysate after dilution of the concentrate into a dialysate. Notably, a solute concentration after dilution into a dialysate can depend on a ratio of a dialysate pump rate to a concentrate pump rate, which in turn, determines a ratio of a dialysate flow rate to a concentrate flow rate. For example, if a ratio of the concentrate flow rate to the dialysate flow rate is 1:250, the concentrations of the solutes in the concentrate solutions will need to be 250 times the desired concentration in the dialysate. The ratio of flow rates of the dialysate pump and concentrate pump can be between any of 100:1 and 300:1, 100:1 and 250:1, 200:1 and 300:1, or 225:1 and 275:1. For example, if the ratio of flow rates of the dialysate pump and concentrate pump are between 200:1 and 300:1, solution 1 in Table 1 can have a concentrate concentration of between 400 mmol/L and 600 mmol/L of potassium, a concentration of between 300 mmol/L and 450 mmol/L of calcium, and a concentration of between 75 mmol/L and 112.5 mmol/L of magnesium. With a ratio of flow rates of the dialysate pump and concentrate pump between 200:1 and 300:1, solution 2 in Table 1 can have a concentrate concentration of between 400 mmol/L and 600 mmol/L of potassium, and a concentration of between 75 mmol/L and 112.5 mmol/L of magnesium. With a ratio of flow rates of the dialysate pump and concentrate pump between 200:1 and 300:1, solution 3 in Table 1 can have a concentrate concentration of between 200 mmol/L and 300 mmol/L of calcium, and a concentration of between 75 mmol/L and 112.5 mmol/L of magnesium. With a ratio of flow rates of the dialysate pump and concentrate pump between 200:1 and 300:1, solution 4 in Table 1 can have a concentrate concentration of between 400 mmol/L and 600 mmol/L of potassium, a concentration of between 300 mmol/L and 450 mmol/L of calcium, a concentration of between 75 mmol/L and 112.5 mmol/L of magnesium, and a concentration of between 400 mmol/L and 600 mmol/L of glucose. With a ratio of flow rates of the dialysate pump and concentrate pump between 200:1 and 300:1, solution 5 in Table 1 can have a concentrate concentration of between 200 mmol/L and 300 mmol/L of potassium, a concentration of between 300 mmol/L and 450 mmol/L of calcium, a concentration of between 75 mmol/L and 112.5 mmol/L of magnesium, and a concentration of between 400 mmol/L and 600 mmol/L of glucose. With a ratio of flow rates of the dialysate pump and concentrate pump between 200:1 and 300:1, solution 6 in Table 1 can have a concentrate concentration of between 600 mmol/L and 900 mmol/L of potassium, a concentration of between 300 mmol/L and 450 mmol/L of calcium, a concentration of between 75 mmol/L and 112.5 mmol/L of magnesium, and a concentration of between 400 mmol/L and 600 mmol/L of glucose. With a ratio of flow rates of the dialysate pump and concentrate pump between 200:1 and 300:1, solution 7 in Table 1 can have a concentrate concentration of between 400 mmol/L and 600 mmol/L of potassium, a concentration of between 75 mmol/L and 112.5 mmol/L of magnesium, and a concentration of between 400 mmol/L and 600 mmol/L of glucose. With a ratio of flow rates of the dialysate pump and concentrate pump between 200:1 and 300:1, solution 8 in Table 1 can have a concentrate concentration of between 200 mmol/L and 300 mmol/L of potassium. With a ratio of flow rates of the dialysate pump and concentrate pump between 200:1 and 300:1, solution 9 in Table 1 can have a concentrate concentration of between 50 mmol/L and 75 mmol/L of calcium. With a ratio of flow rates of the dialysate pump and concentrate pump between 200:1 and 300:1, solution 10 in Table 1 can have a concentrate concentration of between 25 mmol/L and 37.5 mmol/L of magnesium. With a ratio of flow rates of the dialysate pump and concentrate pump between 200:1 and 300:1, solution 11 in Table 1 can have a concentrate concentration of between 200 mmol/L and 300 mmol/L of glucose.

The higher a ratio of flow rates of the dialysate pump to the concentrate pump, the less concentrate will be necessary, thereby allowing a smaller and more compact system relative to known systems. In particular, a concentrate reservoir can be any size including between 500 mL and 1 L. In other embodiments, the concentrate reservoir is 1 L or less, 900 mL or less, 800 mL or less, or 750 mL or less. One of skill in the art will understand that larger or smaller concentrate reservoirs can be used depending on the ratio of flow rates of the dialysate pump and concentrate pump.

The values listed in Table 1 are for illustrative purposes only; other solutions with differing concentrations can be used by the present invention. For example, a base solution can have potassium in a concentration of between 0 and 900 mmol/L, calcium in a concentration of between 0 and 450 mmol/L, magnesium in a concentration of between 37 and 115 mmol/L, and glucose in a concentration of between 0 and 600 mmol/L. The potassium spike solution can result in an increase in dialysate potassium concentration of between 0.5 and 2 mmol/L; an increase in dialysate calcium concentration of between 0.2 and 1 mmol/L; an increase in dialysate magnesium concentration of between 0.1 and 0.3 mmol/L; or an increase in dialysate glucose concentration of between 0.5 and 2 mmol/L.

The counter ions for the cations listed in Table 1 can be any counter ion usable in dialysis including chloride. The resulting concentration of chloride or other counter ions in the dialysate can be determined from the concentrations of the cations listed in Table 1. For example, using base concentrate number 4 in Table 1, the concentration of chloride or other counter ions in the base concentrate can be 5.75 mmol/L. Using base concentrate number 5 in Table 1, the chloride or other counter ion concentration can be 4.75 mmol/L.

The individual components making up the base concentrates and spikes can be provided in prepackaged amounts. The user can combine the prepackaged amounts of the base concentrate and spikes to obtain proper concentrations of each solute in the concentrate solution. Either or both of the base concentrates and spikes can be provided in bulk form, and a user can measure the correct amounts of each of the solutions.

Base concentrates can be packaged and shipped in a solution or powder form. The solution form of the base concentrate can be packaged in a single-use container, non-limiting e.g., >750 mL, or in a bulk solution size, non-limiting e.g., >10 L. If a solution is packaged in bulk, a user can measure and conveniently add only a single-use size bolus to a concentrate reservoir for each dialysis session from the bulk solution. If packaged in a single-use container, the user can conveniently only add the single use-container to the dialysis machine. Alternatively, the base concentrate can be packaged as a powder and formed into a single-use size or a bulk size. A user can dissolve an appropriate amount of powder for each dialysis session as needed. If packaged in bulk, the user can dissolve a required amount of powder for a single-use basis or on a multi-use basis to make either a single-use base concentrate or a multi-use base concentrate. Mixing can be performed directly in the dialysis machine. For example, a user can add a powder into a concentrate reservoir integrated with the dialysis machine. The powder can be dissolved in the concentrate reservoir for single-use or for multi-user. Alternatively, a user can mix the powder in an external reservoir or container, and manually add the resulting mixture to the dialysis machine.

Similar to the base concentrates, spikes can be packaged and shipped in liquid or powder form. The spikes can be packaged in a single size use or in a bulk use size. When packaged and shipped in a single-use size, the user can add the spike(s) to a base concentrate for each use in the concentrate reservoir on the console of the dialysis machine or in an external container. Mixing the spike with the base concentrate in an external container can be preferable to avoid inadvertently mixing solutions of different types. If packaged and shipped in bulk form, a user can add spikes to the base concentrate to create a bulk concentrate, or add spikes to a single-use size of the base concentrate for single-use. Base concentrate and spike amounts can vary depending on cost concerns, therapeutic discretion, and infrastructure support.

Figure 2:
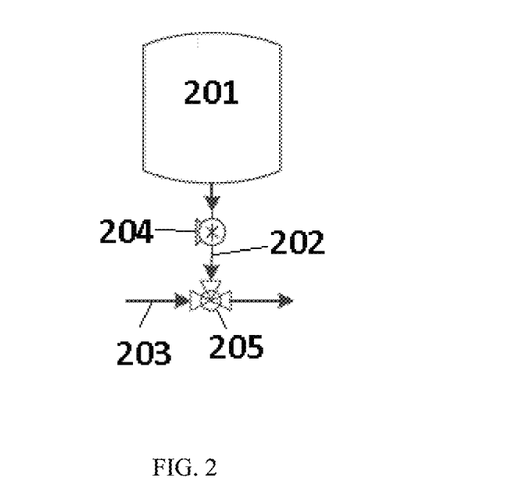
FIG. 2 shows a system for adding concentrates to a dialysate flow path.

FIG. 2 shows components for adding a concentrate to a dialysate flow path. Concentrate reservoir 201 can contain necessary ions and other solutes for addition to the dialysate, such as potassium, calcium, magnesium, acetate and chloride ions, or glucose and other non-ionic solutes. Concentrate reservoir 201 can be fluidly connected to a dialysate flow path 203 through concentrate line 202. Concentrate pump 204 pumps a concentrate from the concentrate reservoir 201, through concentrate line 202 into a dialysate flow path 203. Valve 205 controls the addition of the concentrate from the concentrate reservoir 201 into the dialysate flow path 203. Concentrate pump 204 can include a meter, such as a flow meter, for control over the concentrate flow rate, or the rate at which the concentrate pump 204 pumps fluid from the concentrate reservoir 201 into the dialysate flow path 203. The flow meter may be provided separately on concentrate line 202 and need not be part of the concentrate pump 204.

Figure 3:
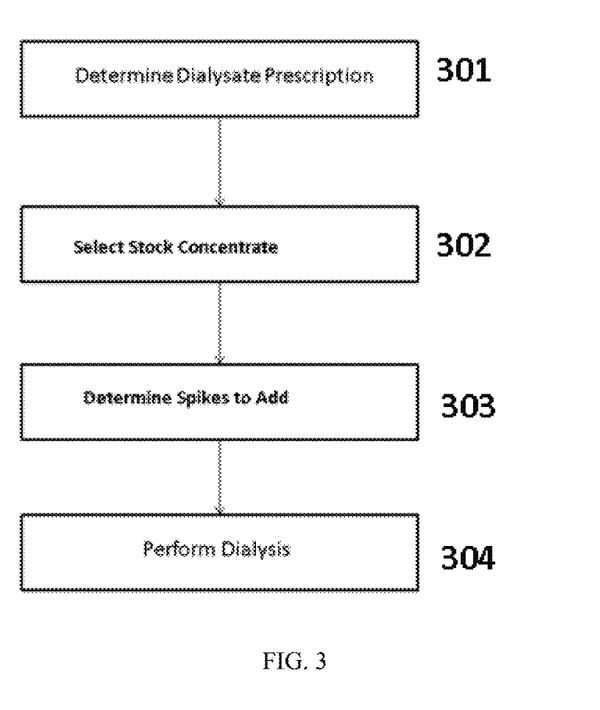
FIG. 3 is a flow chart illustrating the steps in creating a specified dialysate formulation.

FIG. 3 is a flow chart depicting the steps necessary for creating a dialysate with a solute concentration based on a dialysate prescription using the base concentrates and spikes. At step 301, a care-giver can determine an appropriate dialysate prescription for a patient, as described herein. At step 302, a proper base concentrate can be determined. The system can have a processor to determine a proper base concentrate to be used based on the dialysate prescription and available base concentrates. One possible base concentrate can be a base concentrate closest to the dialysate prescription out of all available base concentrates, while having a solute concentration at or below the solute concentration of the dialysate prescription for every solute. In step 303 the type and number of spikes needed to achieve the solute concentration of the dialysate prescription is determined. In step 304, dialysis is carried out, with a concentrate pump rate having a set ratio to the dialysate pump rate, which causes metering in of the cation infusate concentrate at a proper rate to create a dialysate in accordance with the dialysate prescription.

The dialysate prescription can be set by any method known to those or ordinary skill the art. For example, the dialysate prescription can be set based on the concentration of one or more solutes in a patient's blood. If a patient is hyperkalemic, a dialysate prescription with a higher potassium concentration can be set. The dialysate prescription can also be based on a patient outcome from one or more previous dialysis sessions. For example, if during or after a previous dialysis session a particular patient was determined to be hypokalemic, a dialysate prescription with a higher potassium concentration can be used in a later dialysis session.

As described, the proper base concentrates and spikes to be used to achieve a particular dialysate prescription can be determined by a processor. A user can input the dialysate prescription into the processor, and the processor can determine the closest base concentrate available to the dialysate prescription wherein each of the solute concentrations in the dialysate prescription are less than or equal to the post-dilution concentration of the same solutes in the base concentrate. For each solute in the selected base concentrate having a lower post-dilution concentration than the dialysate prescription, the processor can automatically calculate a number of spikes needing to be added to the dialysate to achieve a post-dilution dialysate solute concentration equal to the solute concentration of the dialysate prescription. The system can also have one or more controllers configured to control the pumps and valves making up the customizable dialysate system. The processor can provide instructions to the controllers for operating the pumps and valves as necessary to carry out dialysis with the generated dialysate. For example, the processor can provide instructions to the controllers to control the dialysate pump and concentrate pump so that the flow rates of the dialysate pump and concentrate pump are maintained at a set ratio.

The starting materials for creating the base concentrate and spikes can be within a known range. The concentrations of calcium, magnesium, potassium and acetate ions in the base concentrate and spikes can be within ±5% or ±0.1 mEq/L of an expected concentration. The glucose concentration can be within ±5% or ±0.05 mmol/L of an expected concentration. The concentrations of solutes in the concentrate can be controlled to be within a small range of the expected concentration to ensure the final solute concentration in the dialysate is accurate.

One skilled in the art will understand that various combinations and/or modifications and variations can be made in the described systems and methods depending upon the specific needs for operation. Moreover features illustrated or described as being part of an aspect of the invention may be used in the aspect of the invention, either alone or in combination.

We claim:

1. A method, comprising the steps of:
adding a base concentrate to a concentrate reservoir of a dialysate system wherein the base concentrate contains one or more of potassium, magnesium, calcium, and glucose:
customizing a dialysate by adding one or more spikes to the concentrate reservoir containing the base concentrate wherein the spikes are selected from the group of potassium, magnesium, calcium, glucose, and combinations thereof;
conveying fluid from the concentrate reservoir to a dialysate flow path at a set ratio to obtain a dialysate with a predetermined solute concentration based on a dialysate prescription;
wherein the set ratio is a ratio of a dialysate flow rate to a concentrate flow rate;
sensing a conductivity of dialysate in the dialysate flow path downstream of the concentrate line using a sensor;
determining an actual conductivity of the dialysate;
comparing the actual conductivity of the dialysate to the dialysate prescription; and
if the actual conductivity of the dialysate is lower than the dialysate prescription, adding one or more spikes to the concentrate reservoir.

2. The method of claim 1, wherein the dialysate prescription is determined, at least in part, on a concentration of one or more solutes in a patient's blood.

3. The method of claim 1, wherein the dialysate prescription is determined, at least in part, on a outcome of a patient in one or more previous dialysis sessions.

4. The method of claim 1, wherein the set ratio of the dialysate flow rate to the concentrate flow rate is between any of 100:1 and 300:1, 100:1 and 250:1, 200:1 and 300:1, or 225:1 and 275:1.

5. The method of claim 1, wherein the base concentrate comprises potassium in a concentration of between 0 and 600 mmol/L, calcium in a concentration of between 0 and 900 mmol/L, magnesium in a concentration of between 37 and 115 mmol/L, and glucose in a concentration of between 0 and 600 mmol/L.

6. The method of claim 1, wherein the step of adding one or more spikes to the concentrate reservoir results in any one of:
a) an increase in dialysate potassium concentration of between 0.5 and 2 mmol/L;
b) an increase in dialysate calcium concentration of between 0.2 and 1 mmol/L;
c) an increase in dialysate magnesium concentration of between 0.1 and 0.3 mmol/L; or
d) an increase in dialysate glucose concentration of between 0.5 and 2 mmol/L.

7. The method of claim 1, wherein the step of adding one or more spikes to the concentrate reservoir comprises adding one or more powders to the concentrate reservoir.

8. The method of claim 1, wherein the step of adding one or more spikes to the concentrate reservoir comprises adding one or more spike solutions to the concentrate reservoir.

9. The method of claim 1, wherein the step of adding a base concentrate to the concentrate reservoir comprises adding a base solution to the concentrate reservoir.

10. The method of claim 1, wherein the step of adding a base concentrate to the concentrate reservoir comprises dissolving a base powder in water.

11. A dialysis system, comprising:
- a concentrate reservoir configured to contain a base concentrate solution wherein the concentrate reservoir is configured to receive one or more spikes and is fluidly connected to a dialysate flow path via a concentrate line, wherein the base concentrate contains one or more of potassium, magnesium, calcium, and glucose and wherein the spikes are selected from the group of potassium, magnesium, calcium, glucose, and combinations thereof;
- a concentrate pump for conveying fluid from the concentrate reservoir to the dialysate flow path; and
- a conductivity sensor in the dialysate flow path downstream of the concentrate line wherein the conductivity sensor determines a conductivity of dialysate in the dialysate flow path;
- wherein the system provides instructions to add one or more spikes to the concentrate reservoir if the concentration of any one or more of magnesium, calcium, potassium, or glucose in the dialysate flow path is less than dialysate prescription.

12. The dialysis system of claim 11, further comprising a processor for performing the method of claim 1.

13. The dialysis system of claim 11, wherein the dialysate flow path comprises a dialysate pump; and wherein a ratio of flow rates of the dialysate pump and concentrate pump is a set ratio.

14. The dialysis system of claim 13, wherein the ratio of flow rates of the dialysate pump and concentrate pump is between any of 100:1 and 300:1, 100:1 and 250:1, 200:1 and 300:1, or 225:1 and 275:1.

15. The dialysis system of claim 11, wherein the system provides an alert if the conductivity of the dialysate in the dialysate flow path differs from a dialysate prescription.

* * * * *